United States Patent
Nunley et al.

(10) Patent No.: US 9,468,535 B2
(45) Date of Patent: Oct. 18, 2016

(54) INTERBODY SPACER

(75) Inventors: Pierce Nunley, Shreveport, LA (US); Brandon Moore, Summit Point, WV (US); Stephanie Volk, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 271 days.

(21) Appl. No.: 13/270,568

(22) Filed: Oct. 11, 2011

(65) Prior Publication Data

US 2012/0158062 A1   Jun. 21, 2012

Related U.S. Application Data

(60) Provisional application No. 61/424,181, filed on Dec. 17, 2010.

(51) Int. Cl.
   *A61F 2/44*   (2006.01)
   *A61F 2/46*   (2006.01)
   *A61F 2/30*   (2006.01)

(52) U.S. Cl.
   CPC ........... *A61F 2/4455* (2013.01); *A61F 2/4465* (2013.01); *A61F 2/4611* (2013.01); *A61F 2002/308* (2013.01); *A61F 2002/30126* (2013.01); *A61F 2002/30285* (2013.01); *A61F 2002/30617* (2013.01); *A61F 2002/30797* (2013.01); *A61F 2002/30879* (2013.01); *A61F 2002/4475* (2013.01); *A61F 2002/4627* (2013.01); *A61F 2002/4629* (2013.01); *A61F 2310/00023* (2013.01); *A61F 2310/00029* (2013.01); *A61F 2310/00131* (2013.01); *A61F 2310/00359* (2013.01)

(58) Field of Classification Search
   USPC ............................................ 623/17.11–17.16
   See application file for complete search history.

(56) References Cited

U.S. PATENT DOCUMENTS

| | | | |
|---|---|---|---|
| 5,053,036 A | 10/1991 | Perren et al. | |
| 5,290,312 A * | 3/1994 | Kojimoto et al. | ......... 623/17.15 |
| 5,520,690 A | 5/1996 | Errico et al. | |
| 5,534,030 A * | 7/1996 | Navarro et al. | ........... 623/17.15 |
| 5,766,252 A * | 6/1998 | Henry | .................. A61F 2/4455 |
| | | | 606/247 |
| 5,904,683 A | 5/1999 | Pohndorf et al. | |
| 6,099,531 A | 8/2000 | Bonutti | |
| 6,342,074 B1 | 1/2002 | Simpson | |
| 6,364,880 B1 | 4/2002 | Michelson | |
| 6,423,063 B1 | 7/2002 | Bonutti | |
| 6,558,423 B1 | 5/2003 | Michelson | |
| 6,629,998 B1 | 10/2003 | Lin | |
| 6,716,214 B1 | 4/2004 | Jackson | |
| 6,972,019 B2 | 12/2005 | Michelson | |
| 6,984,234 B2 | 1/2006 | Bray | |
| 7,001,385 B2 | 2/2006 | Bonutti | |
| 7,018,412 B2 * | 3/2006 | Ferreira et al. | ............ 623/17.11 |
| 7,033,394 B2 | 4/2006 | Michelson | |

(Continued)

*Primary Examiner* — Jan Christopher Merene
(74) *Attorney, Agent, or Firm* — Carter, DeLuca, Farrell & Schmidt, LLP

(57) ABSTRACT

An intervertebral implant includes a body portion defining a longitudinal axis. The body portion includes a distal end portion, a proximal end portion, anterior and posterior walls that extend between the distal and proximal end portions, and top and bottom surfaces. At least one of the top and bottom surfaces includes a plurality of substantially concentrically arranged ridges configured and adapted to engage vertebral bodies. In particular, the plurality of substantially concentrically arranged ridges are a plurality of ring-shaped protrusions that define a generally saw-tooth pattern in a radial direction.

16 Claims, 5 Drawing Sheets

(56) References Cited

U.S. PATENT DOCUMENTS

| | | |
|---|---|---|
| 7,041,135 B2 | 5/2006 | Michelson |
| 7,052,499 B2 | 5/2006 | Steger et al. |
| 7,077,864 B2 | 7/2006 | Byrd, III et al. |
| 7,175,624 B2 | 2/2007 | Konieczynski et al. |
| 7,229,443 B2 | 6/2007 | Eberlein et al. |
| 7,318,825 B2 | 1/2008 | Butler et al. |
| 7,618,456 B2 | 11/2009 | Mathieu et al. |
| 7,651,517 B2 | 1/2010 | Konieczynski et al. |
| 7,811,292 B2* | 10/2010 | Lo et al. .................. 606/99 |
| 7,862,616 B2 | 1/2011 | Lechmann et al. |
| 8,496,707 B2* | 7/2013 | Adamo ................. 623/17.14 |
| 2001/0021851 A1 | 9/2001 | Eberlein et al. |
| 2002/0128654 A1 | 9/2002 | Steger et al. |
| 2003/0040802 A1* | 2/2003 | Errico et al. ............. 623/17.14 |
| 2003/0069640 A1* | 4/2003 | Ferreira et al. ........... 623/17.11 |
| 2003/0105527 A1* | 6/2003 | Bresina ..................... 623/17.16 |
| 2003/0130737 A1 | 7/2003 | McGahan et al. |
| 2003/0135276 A1* | 7/2003 | Eckman ................... 623/17.11 |
| 2004/0127990 A1* | 7/2004 | Bartish et al. ........... 623/17.11 |
| 2004/0230305 A1* | 11/2004 | Gorensek ............... A61F 2/446<br>623/17.11 |
| 2005/0038511 A1* | 2/2005 | Martz et al. ............. 623/17.11 |
| 2005/0143822 A1* | 6/2005 | Paul ..................... A61F 2/4455<br>623/17.16 |
| 2006/0217807 A1* | 9/2006 | Peterman et al. ......... 623/17.11 |
| 2007/0073298 A1 | 3/2007 | Beutter et al. |
| 2007/0100452 A1* | 5/2007 | Prosser ................. A61F 2/4465<br>623/17.11 |
| 2007/0219635 A1 | 9/2007 | Mathieu et al. |
| 2007/0233263 A1* | 10/2007 | Melkent et al. ........... 623/17.16 |
| 2007/0282441 A1* | 12/2007 | Stream et al. ............ 623/17.11 |
| 2007/0293948 A1* | 12/2007 | Bagga et al. ............ 623/17.11 |
| 2008/0249624 A1 | 10/2008 | Josimovic-Alasevic et al. |
| 2008/0249625 A1 | 10/2008 | Waugh et al. |
| 2008/0288076 A1* | 11/2008 | Soo et al. .................. 623/17.16 |
| 2009/0157187 A1* | 6/2009 | Richelsoph ............... 623/17.16 |
| 2009/0198339 A1* | 8/2009 | Kleiner et al. ............ 623/17.16 |
| 2009/0276049 A1* | 11/2009 | Weiland .................... 623/17.16 |
| 2009/0299479 A1* | 12/2009 | Jones et al. ............... 623/17.16 |
| 2010/0087925 A1* | 4/2010 | Kostuik et al. ............ 623/17.16 |
| 2010/0137919 A1 | 6/2010 | Wolter |
| 2011/0045087 A1* | 2/2011 | Kerr et al. .................. 424/490 |
| 2011/0230965 A1* | 9/2011 | Schell .................... A61F 2/447<br>623/17.16 |
| 2011/0301710 A1* | 12/2011 | Mather et al. ............. 623/17.16 |
| 2012/0022654 A1* | 1/2012 | Farris et al. .............. 623/17.16 |
| 2012/0065613 A1* | 3/2012 | Pepper et al. ............. 604/500 |
| 2012/0310351 A1* | 12/2012 | Farley .................... A61F 2/442<br>623/17.16 |

* cited by examiner

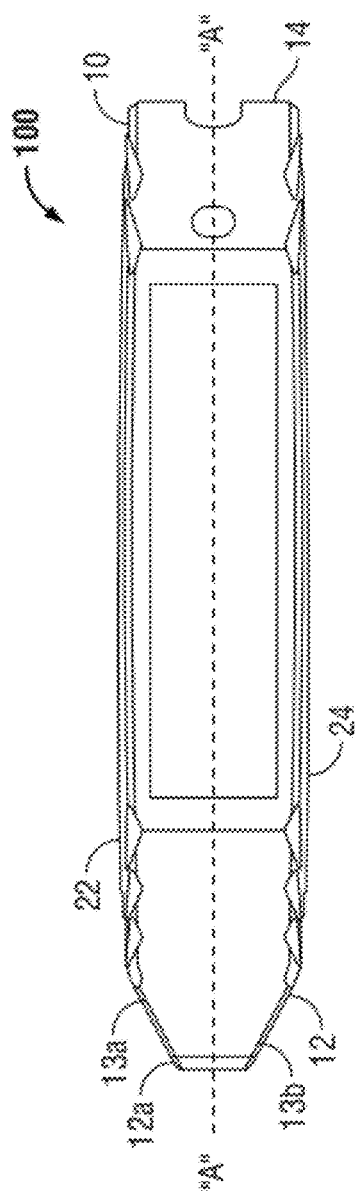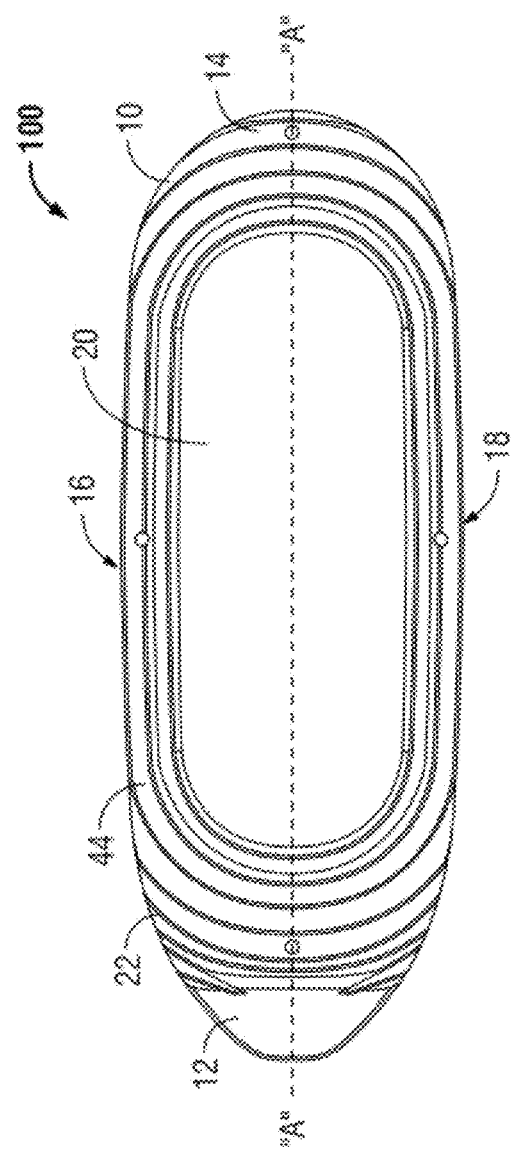

INTERBODY SPACER

CROSS-REFERENCE TO RELATED APPLICATION

This application claims priority to, and the benefit of, U.S. Provisional Patent Application No. 61/424,181, filed on Dec. 17, 2010, the entire contents of which are hereby incorporated by reference herein.

BACKGROUND

1. Technical Field

The present disclosure relates to an apparatus for treating spinal conditions, and more particularly, to an intervertebral implant and a method of use therefor.

2. Background of Related Art

The human spinal column is a highly complex structure. It includes twenty-four discrete bones, known as vertebrae, coupled sequentially to one another to house and protect critical elements of the nervous system. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina.

The vertebrae are separated and cushioned by thin pads of tough, resilient fiber known as inter-vertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

For many reasons, such as aging and trauma, the intervertebral discs can begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. After a partial or complete discectomy, the normally occupied space between adjacent vertebral bodies is subject to collapse and/or misalignment due to the absence of all or part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged and moved from their desired implantation location due to movement by the patient before sufficient bone growth has occurred.

Therefore a need exists for a spinal implant that resists dislocation from the implantation site, while allowing for bone growth between the adjacent vertebrae and resisting subsidence into the vertebral body end plates.

SUMMARY

In accordance with an embodiment of the present disclosure, there is provided an intervertebral implant including a body portion defining a longitudinal axis. The body portion includes a distal end portion, a proximal end portion, anterior and posterior walls that extend between the distal and proximal end portions, and top and bottom surfaces that are configured and adapted to engage vertebral bodies. In particular, at least one of the top and bottom surfaces includes a plurality of substantially concentrically arranged ridges.

In an embodiment, the plurality of concentrically arranged ridges may be a plurality of ring-shaped protrusions that define a generally saw-tooth pattern in a radial direction. The body portion may define a cavity configured and adapted to retain bone graft material. The proximal end portion may define a recess configured and adapted to engage an implant insertion device. The proximal end portion may have a convex surface adapted to engage the implant insertion device. The convex surface of the proximal end portion may define a threaded aperture aligned with the longitudinal axis of the body. The threaded aperture may be adapted to threadably engage the implant insertion device.

In another embodiment, the distal end portion may include a rounded nose portion tapered between the anterior and posterior walls. The rounded nose portion may be tapered between the top and bottom surfaces. The top and bottom surfaces may be substantially parallel. In addition, the anterior and posterior walls may have substantially the same width. Moreover, the anterior and posterior walls may be substantially parallel.

The anterior and posterior walls may define a relief feature configured and adapted for use with an insertion or removal instrument to insert or remove the intervertebral implant from the surgical site.

In an embodiment, the anterior and posterior walls may each be defined by a transition portion, a first sloped portion extending between the transition portion and the distal end portion of the body portion, and a second sloped portion extending between the transition portion and the proximal end portion of the body portion. The height of the posterior wall may be different than that of the anterior wall.

In accordance with another aspect of the present disclosure, there is provided a method of securing adjacent vertebral bodies including providing an intervertebral implant. The intervertebral implant includes a body portion including top and bottom surfaces that are configured and adapted to engage vertebral bodies. At least one of the top and bottom surfaces includes a plurality of substantially concentrically arranged ridges. The method further includes distracting adjacent vertebral bodies and inserting the intervertebral implant between the vertebral bodies.

In an embodiment, the method may further include removing vertebral tissue. In addition, the method may further include placing bone graft in the cavity of the body portion. In another embodiment, inserting the intervertebral implant between the vertebral bodies may include inserting the intervertebral implant from a lateral approach.

The plurality of substantially concentrically arranged ridges may be a plurality of ring-shaped protrusions that define a generally saw-tooth pattern in a radial direction. The body portion may define a cavity extending between the top and bottom surfaces. Advantageously, the substantially concentrically arranged ridges provide stability against fore and aft, oblique or side to side movement of the intervertebral implant within the disc space.

BRIEF DESCRIPTION OF THE DRAWINGS

Various embodiments of the present disclosure are described hereinbelow with reference to the drawings, wherein:

FIG. 2 is a side view of the interbody spacer of FIG. 1;

FIG. 3 is a top, plan view of the interbody spacer of FIG. 1;

DETAILED DESCRIPTION OF EMBODIMENTS

Figure 1:
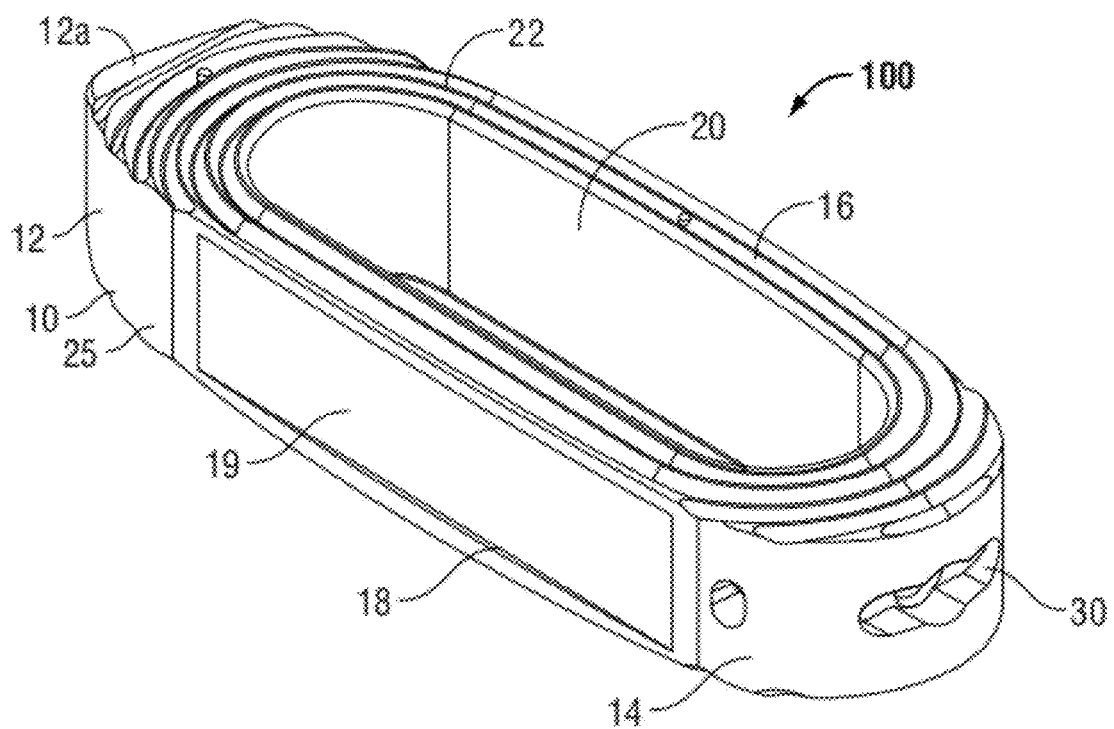
FIG. 1 is a perspective view of an interbody spacer in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIG. 1, an embodiment of the present disclosure is shown generally as an interbody spacer 100 configured and adapted to be positionable between adjacent vertebral bodies to support the vertebral bodies and to promote spinal fusion. Interbody spacer 100 may be made of titanium, titanium alloy, stainless steel, allograft bone, autologous bone graft, polyetheretherketone (PEEK), polysulfone (RADEL), polyetherimide (ULTEM), cobalt chrome, polymeric materials, a combination thereof, or any other suitable biocompatible material. In particular, interbody spacer 100 may be formed of bone, or an artificial material other than bone, which may be harder or stronger than bone, such as, e.g., ceramic materials. Interbody spacer 100 may include a bone growth promoting material such as, e.g., bone morphogenic protein and hydroxyapatite. Spacer 100 may be fabricated from multiple components. Alternatively, interbody spacer 100 may be formed monolithically as a single construct.

Figure 4:
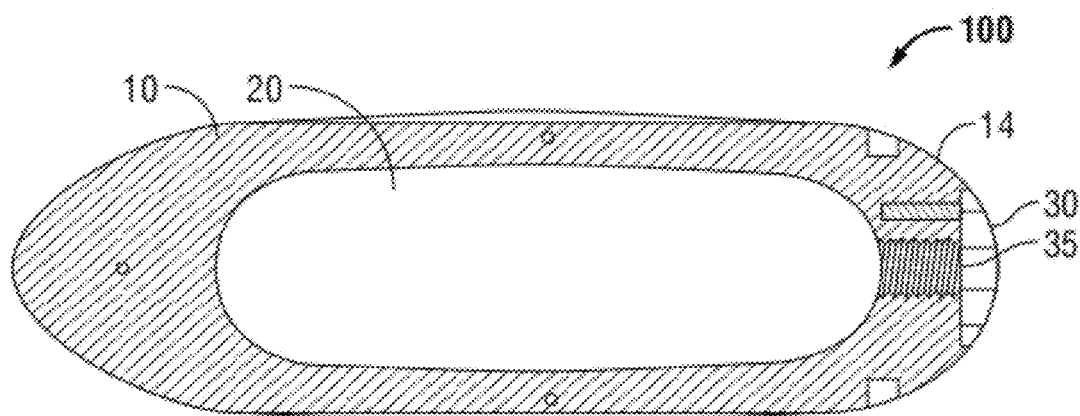
FIG. 4 is a longitudinal cross-sectional view of the interbody spacer of FIG. 3.

With reference now to FIGS. 1 and 2, interbody spacer 100 includes a body portion 10 defining a longitudinal axis A-A. Body portion 10 includes a distal end 12, a proximal end 14, and anterior and posterior walls 16, 18 that extend between the distal and proximal ends 12, 14. Body portion 10 further includes a top surface 22 and a bottom surface 24. Body portion 10 defines a through hole 20 configured and adapted for containment of additional bone graft material to facilitate fusion. Proximal end 14 of body portion 10 is a generally convex surface defining a recess 30 defining a threaded aperture 35 (FIG. 4) aligned with the longitudinal axis "A-A." Threaded aperture 35 is adapted to engage an insertion instrument 50 (FIG. 6), as will be described below.

With continued reference to FIG. 2, distal end 12 includes a rounded nose portion 12a including first and second contoured surfaces 13a, 13b that lead to top and bottom surfaces 22, 24, respectively. The opposing contoured surfaces 13a, 13b) define a torpedo-shaped tip profile that facilitates insertion of interbody spacer 100 into the disc space. Furthermore, such profile enables interbody spacer 100 to be utilized to distract the disc space. In addition, distal end 12 further includes a substantially contoured side surface 25 (FIG. 1) that connects anterior and posterior walls 16, 18. Side surface 25 is tapered with respect to longitudinal axis "A-A" to facilitate insertion thereof through the disc space.

Top and bottom surfaces 22, 24 are substantially parallel. In addition, anterior and posterior walls 16, 18 that extend between proximal end 14 and distal end 12 are also substantially parallel. In particular, anterior and posterior walls 16, 18 provide a relief feature 19 (FIG. 1) that is configured and adapted for use with an insertion or removal instrument to easily insert or remove interbody spacer 100 to and from the surgical site.

With reference now to FIG. 3, through hole 20 is concentrically defined with body portion 10 and is symmetric with respect to longitudinal axis "A-A," whereby the thickness of the respective anterior and posterior walls 16, 18 are substantially identical. Moreover, the thickness of each of anterior and posterior walls 16, 18 is substantially uniform over the respective lengths thereof.

Figure 5:
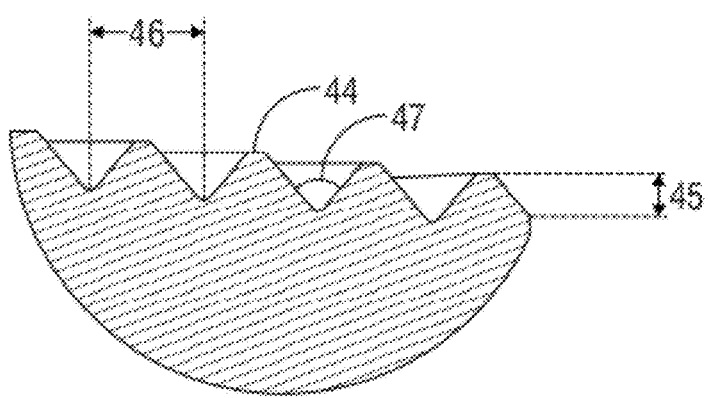
FIG. 5 is a partial side cross-sectional view of a top surface of the interbody spacer of FIG. 4.

Top and bottom surfaces 22, 24 of body portion 10 are configured and adapted to engage endplates of superior and inferior vertebral bodies, respectively. Each of top and bottom surfaces 22, 24 define ridges or similar projections to aid in securing interbody spacer 100 to the vertebral bodies for enhanced gripping of vertebral bodies and stability against fore and aft, oblique or side to side movement of interbody spacer 100 within the disc space. In particular, each top and bottom surface 22, 24 defines a plurality of ring-shaped protrusions 44 that define a generally saw-tooth pattern in a radial direction. The plurality of ring-shaped protrusions 44 are concentrically arranged with through hole 20. For example, each ring-shaped protrusion 44 has a height 45 of about 0.030 inches and a width 46 of about 0.062 inches with 80-degree crest-to-crest angle 47, as shown in FIG. 5.

With continued reference to FIG. 3, ring-shaped protrusions 44 are concentrically arranged with through hole 20 and are symmetrically arranged with respect to longitudinal axis "A-A." For example, ring-shaped protrusions 44 on respective top and bottom surfaces 22, 24 have a radius of curvature of approximately 70 inches and ring-shaped protrusions 44 in a peripheral portions of body portion 10 including distal end 12 and proximal end 14 have a radius of curvature of approximately 4.3 inches. Under such dimensions, ring-shape protrusions 44 in the peripheral portion of body portion 10 and on respective top and bottom surfaces 22, 24 define a substantially elliptical pattern. It is contemplated that the thickness of anterior and/or posterior walls 16, 18 may be varied, which in turn may vary the radius of curvature of ring-shaped protrusions 44.

It is further contemplated that interbody spacer 100 may include tantalum markers to aid visualization of interbody spacer 100 during image guidance, such as fluoroscopy. It is also envisioned that the dimensions of interbody spacer 100 may be tailored to the vertebral body anatomy of the patient. For example, the height of interbody spacer 100 ranges from about 5 mm to 20 mm, and the length ranges from about 50 to 200 mm with the width ranging from about 10 mm to 80 mm.

Figure 6:
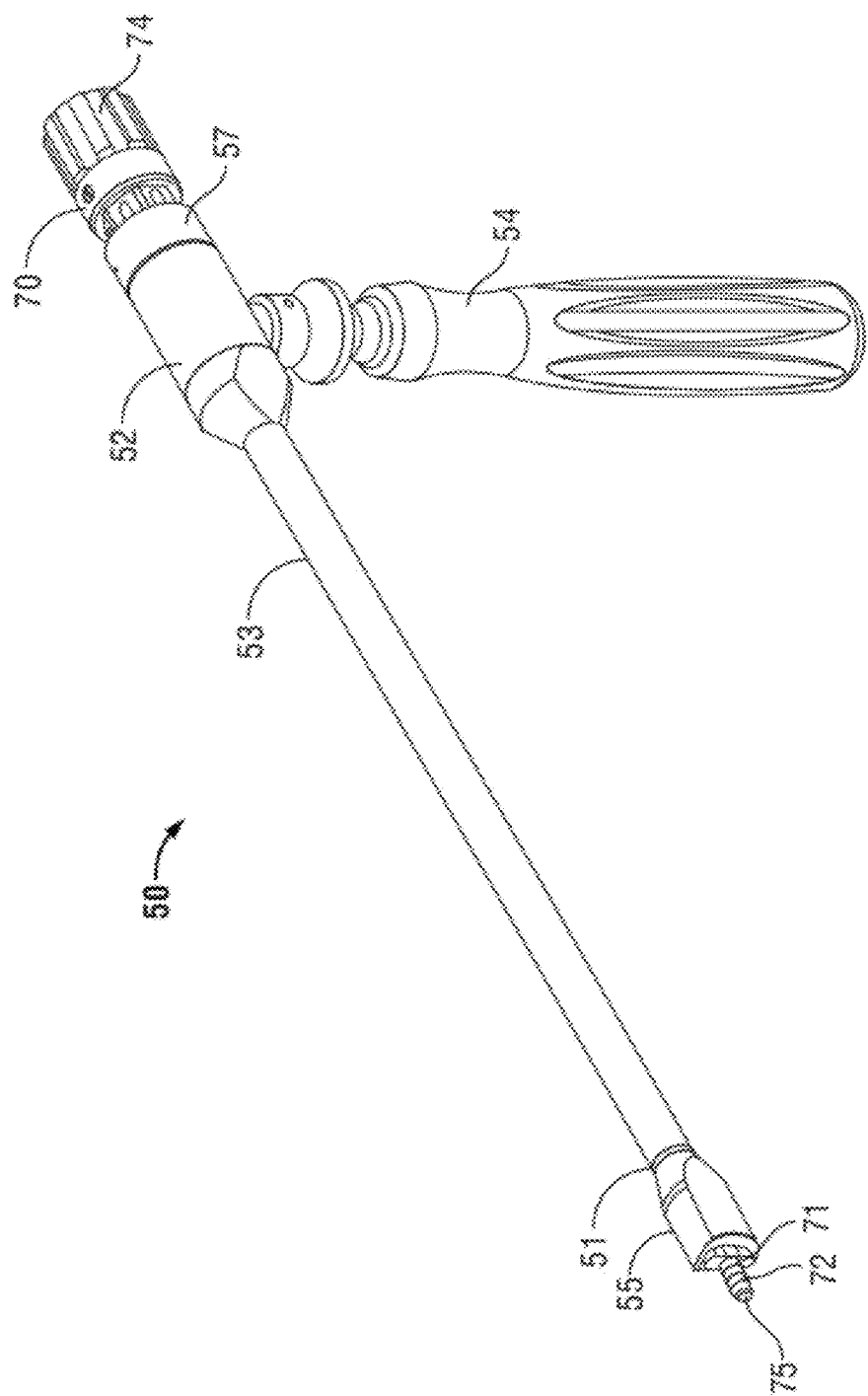
FIG. 6 is a perspective view of an inserter instrument for use with the interbody spacer of FIG. 1.

With reference to FIG. 6, insertion instrument 50 may be utilized to insert interbody spacer 100 between vertebral bodies. Insertion instrument 50 includes a housing 52 having a tubular member 53 extending therefrom. A handle 54 extends from housing 52 and is orthogonal to tubular member 53. A coupling 55 is disposed at a distal end 51 of tubular member 53 and has a concaved profile configured and adapted for mating with arcuate proximal end 14 of interbody spacer 100. A lumen (not shown) extends from distal end 51 of coupling 55 to a proximal end 57 of housing 52. Inserter rod 70 is repositionable through housing 52 and tubular member 53. Inserter rod 70 has a threaded portion 72 at its distal end 71 that is configured for threadably engaging threaded aperture 35 of interbody spacer 100. A knob 74 is disposed in opposition to threaded portion 72 with a shaft 75 extending therebetween.

In use, the surgeon uses fluoroscopy or another imaging modality to identify the correct operative level and makes one or more incisions through the patient's skin using conventional instruments. The number and type of incisions made (e.g. transverse or vertical) is related to the procedure to be performed. After the surgeon determines the appropriate type and size of interbody spacer 100, insertion instrument 50 is threaded into threaded aperture 35 of interbody spacer 100. Inserter rod 70 and handle 54 are coupled together and the selected spinal interbody spacer 100 is threaded on distal end 71 of inserter rod 70 adjacent coupling 55 of distal end 51 of tubular member 53. This provides a rigid connection between insertion instrument 50 and interbody spacer 100. A mallet and slap hammer (not shown) may also be used to facilitate placement of interbody spacer 100. If needed, the surgeon may place various types of bone graft into through hole 20 prior to insertion in order to help facilitate the fusion process. Interbody spacer 100 is then inserted into the prepared disc space and placed such that round nose portion 12a is inserted first for ease of insertion and rests on the distal apophyseal ring of the vertebral body, and thereby allowing proximal end 14 to reside on the proximal apophyseal ring of the vertebral body. By residing on the apophyseal ring, interbody spacer 100 is less likely to experience subsidence into the end plates which will facilitate fusion between the vertebral bodies. The implant disclosed herein is suitable for use in the procedure described in co-pending U.S. patent application filed on Oct. 10, 2011, titled "Lateral Access System and Method of Use," the contents of which are hereby incorporated by reference.

Figure 7:
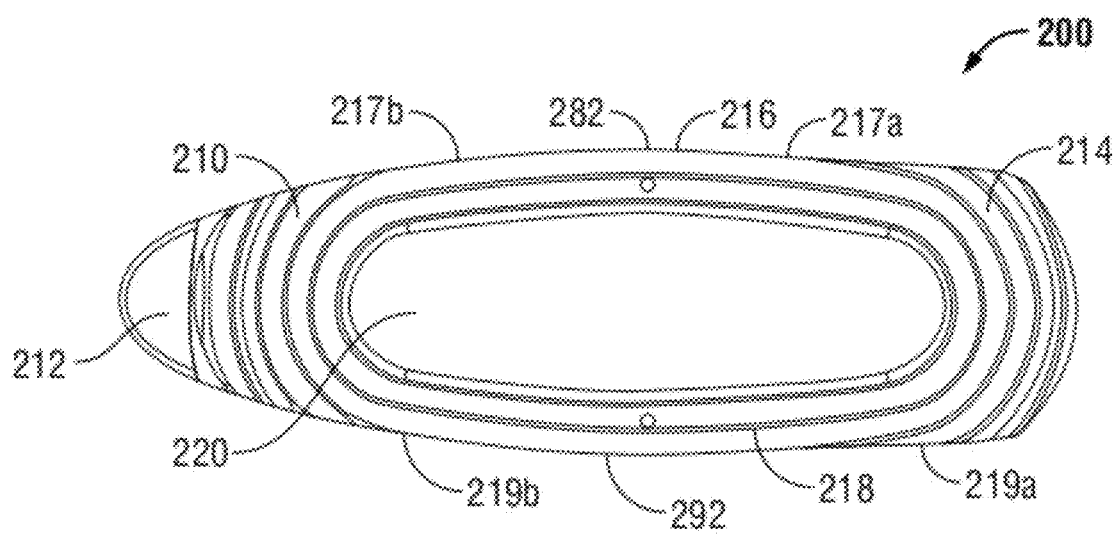
FIG. 7 is a top view of an interbody spacer in accordance with another embodiment of the present disclosure.
Figure 8:
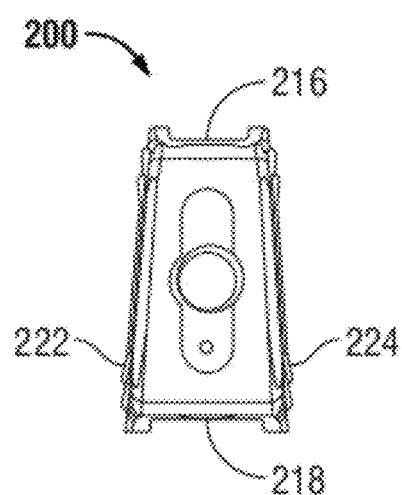
FIG. 8 is a rear view of the interbody spacer of FIG. 7.

With reference now to FIGS. 7 and 8, another embodiment of an interbody spacer 200 is illustrated. In the interest of brevity, the present embodiment will focus on the differences between the previously described interbody spacer 100 and interbody spacer 200. Interbody spacer 200 is configured and adapted to be positionable between the vertebral bodies to support the vertebral bodies and to promote spinal fusion.

Interbody spacer 200 includes a body portion 210 including a distal end portion 212, a proximal end portion 214, an anterior wall 216, and a posterior wall 218 that define a top surface 222 and a bottom surface 224. Moreover, body portion 210 defines a through hole 220 for containment of additional bone graft material to facilitate fusion. Anterior wall 216 is defined by a transition portion 282, a first sloped portion 217a extending between proximal end portion 214 and transition portion 282 and a second sloped portion 217b extending between transition portion 282 and distal end portion 212. Posterior wall 218 is defined by a transition portion 292, a first sloped portion 219a extending between proximal end portion 214 and transition portion 292 and a second sloped portion 219b extending between transition portion 292 and distal end portion 212. In particular, first and second sloped portions 217a, 217b, 219a, 219b each define a slope having a linear (i.e., a non-curvature) surface. In addition, transition portions 282, 292 may be a point or a plane.

With particular reference to FIG. 8, anterior wall 216 and posterior wall 218 have substantially identical thicknesses. However, posterior wall 218 has a larger height than that of anterior wall 216, whereby interbody spacer 200 has a lordotic configuration. In addition, top and bottom surfaces 222, 224 each define a plurality of ring-shaped protrusions 244 that define a generally saw-tooth pattern in a radial direction, as described hereinabove.

Although the illustrative embodiments of the present disclosure have been described herein with reference to the accompanying drawings, the above description, disclosure, and figures should not be construed as limiting, but merely as exemplifications of particular embodiments. By way of example only, it is contemplated that one or more of the concentric protrusions on the top or bottom surface of the implant may be discontinuous while still defining a substantially ring-shaped ridge. It is to be understood, therefore, that the disclosure is not limited to those precise embodiments, and that various other changes and modifications may be effected therein by one skilled in the art without departing from the scope or spirit of the disclosure.

What is claimed is:

1. An intervertebral implant comprising:
   a body portion defining a central longitudinal axis, the body portion including a distal end portion, a proximal end portion, anterior and posterior walls that extend between the distal and proximal end portions, and top and bottom surfaces configured and adapted to engage vertebral bodies, the anterior and posterior walls extending between the top and bottom surfaces of the body portion, each of the distal and proximal end portions including an arcuate portion, each of the anterior and posterior walls including a transition portion disposed between the arcuate portions of the respective distal and proximal end portions, wherein at least one of the top and bottom surfaces includes a plurality of substantially concentrically arranged ridges that define an elliptical pattern, and each of the anterior and posterior walls includes a first, planar sloped portion extending between the arcuate portion of the proximal end portion and the transition portion and a second, planar sloped portion extending between the transition portion and the arcuate portion of the distal end portion, wherein the first and second planar sloped portions define an acute angle with respect to the central longitudinal axis of the body portion, and wherein a first of the plurality of concentrically arranged ridges defines an uninterrupted ridge towards a center of the intervertebral implant and a second of the plurality of concentrically arranged ridges defines an interrupted ridge away from the center of the intervertebral implant.

2. The intervertebral implant according to claim 1, wherein the plurality of substantially concentrically arranged ridges are a plurality of ring-shaped protrusions that define a generally saw-tooth pattern in a radial direction.

3. The intervertebral implant according to claim 2, wherein the height of the posterior wall is different than that of the anterior wall.

4. The intervertebral implant according to claim 1, wherein the body portion defines a cavity configured and adapted to retain bone graft material.

5. The intervertebral implant according to claim 1, wherein the proximal end portion defines a recess configured and adapted to engage an implant insertion device.

6. The intervertebral implant according to claim 5, wherein the proximal end portion has a convex surface adapted to engage the implant insertion device.

7. The intervertebral implant according to claim 6, wherein the convex surface of the proximal end portion defines an aperture aligned with the central longitudinal axis of the body portion, the aperture adapted to threadably engage the implant insertion device.

8. The intervertebral implant according to claim 1, wherein the distal end portion includes a rounded nose portion tapered between the anterior and posterior walls.

9. The intervertebral implant according to claim 8, wherein the rounded nose portion is tapered between the top and bottom surfaces.

10. The intervertebral implant according to claim 1, wherein the top and bottom surfaces are substantially parallel.

11. The intervertebral implant according to claim 1, wherein the anterior and posterior walls have substantially the same width.

12. The intervertebral implant according to claim 1, wherein the anterior and posterior walls define a relief feature configured and adapted for use with an insertion or removal instrument to insert or remove the intervertebral implant to or from a surgical site.

13. The intervertebral implant according to claim 1, wherein the body portion has an elongated shape.

14. The intervertebral implant according to claim 1, wherein a length of the body portion from the proximal end portion to the distal end portion is greater than a width of the body portion from the transition portion of the anterior wall to the transition portion of the posterior wall.

15. The intervertebral implant according to claim 1, wherein the first sloped portion of the anterior wall and the first sloped portion of the posterior wall define a first distance between the respective transition portions and define a second distance between the respective proximal portions, wherein the first distance is greater than the second distance.

16. An intervertebral implant comprising:
a body portion defining a central longitudinal axis, the body portion including:
a distal end portion;
a proximal end portion;
anterior and posterior walls that extend between the distal and proximal end portions, each of the anterior and posterior walls including a transition portion;
a first sloped portion extending from the proximal end portion to the transition portion; and
a second sloped portion extending from the transition portion to the distal end portion, and top and bottom surfaces configured and adapted to engage vertebral bodies,
wherein at least one of the top and bottom surfaces includes a plurality of substantially concentrically arranged ridges, wherein the distal end portion includes a rounded nose portion tapered between the anterior and posterior walls and between the top and bottom surfaces,
wherein the first and second sloped portions are non-parallel with respect to the central longitudinal axis of the body portion,
wherein the plurality of concentrically arranged ridges define an elliptical pattern, and wherein a first of the plurality of concentrically arranged ridges defines an uninterrupted ridge towards a center of the intervertebral implant and a second of the plurality of concentrically arranged ridges defines an interrupted ridge away from the center of the intervertebral implant.

* * * * *